United States Patent [19]

Friese et al.

[11] Patent Number: 5,505,837

[45] Date of Patent: Apr. 9, 1996

[54] SENSOR ARRANGEMENT FOR DETERMINING GAS COMPONENTS AND/OR GAS CONCENTRATIONS OF GAS MIXTURES

[75] Inventors: Karl-Hermann Friese, Leonberg; Hermann Dietz; Werner Gruenwald, both of Gerlingen; Gerhard Hoetzel, Stuttgart; Harald Neumann, Vaihingen/Enzweihingen; Johann Riegel, Bietigheim-Bissingen; Bernd Schumann, Rutesheim, all of Germany

[73] Assignee: Robert Bosch GmbH, Stuttgart, Germany

[21] Appl. No.: 290,704

[22] PCT Filed: Mar. 17, 1994

[86] PCT No.: PCT/DE94/00289

§ 371 Date: Dec. 12, 1994

§ 102(e) Date: Dec. 12, 1994

[87] PCT Pub. No.: WO94/24550

PCT Pub. Date: Oct. 27, 1994

[30] Foreign Application Priority Data

Apr. 10, 1993 [DE] Germany ............... 43 11 851.8

[51] Int. Cl.[6] ................................................. G01N 27/26
[52] U.S. Cl. .................... 204/425; 204/426; 204/427; 204/429; 204/408
[58] Field of Search ........................... 204/425, 426, 204/427, 429, 424, 408

[56] References Cited

U.S. PATENT DOCUMENTS 4,905,652  3/1990  Nakajima et al. ................. 204/425

4,927,517  5/1990  Mizutani et al. .................. 204/406

FOREIGN PATENT DOCUMENTS 0259175  3/1988  European Pat. Off. .
0517364  12/1992  European Pat. Off. .
3707874  9/1987  Germany .
3728618  3/1988  Germany .

OTHER PUBLICATIONS

Visser et al.: "Sensors for measuring combustibles in the absence of oxygen". In: Sensors and Actuators B., 9, 1992, Lausanne, CH, pp. 233–239. No month available.

Suzuki et al.: "Air–Fuel Ratio Sensor for Rich, Stoichiometric and Lean Ranges". In: SAE Technical Paper Series, Int. Congress and Exposition, Detroit, Michigan, Feb. 24–29, 1986.

Primary Examiner—Bruce F. Bell
Attorney, Agent, or Firm—Spencer & Frank

[57] ABSTRACT

A sensor arrangement for determining at least one of gas components and gas concentrations of gas mixtures including CO, $NO_x$ and HC in exhaust gases of internal combustion engines, includes a measuring element which has a sensitive region; and a pump cell that includes a solid electrolyte and inner and outer pump electrodes which are opposingly disposed at least on the solid electrolyte and which effect an oxygen transfer to the measuring element, wherein the pump cell and the measuring element are spatially separated from one another, are located in different temperature zones during operation of the sensor arrangement, and are connected to one another by a diffusion segment through which oxygen can diffuse from the pump cell to the measuring element.

18 Claims, 5 Drawing Sheets

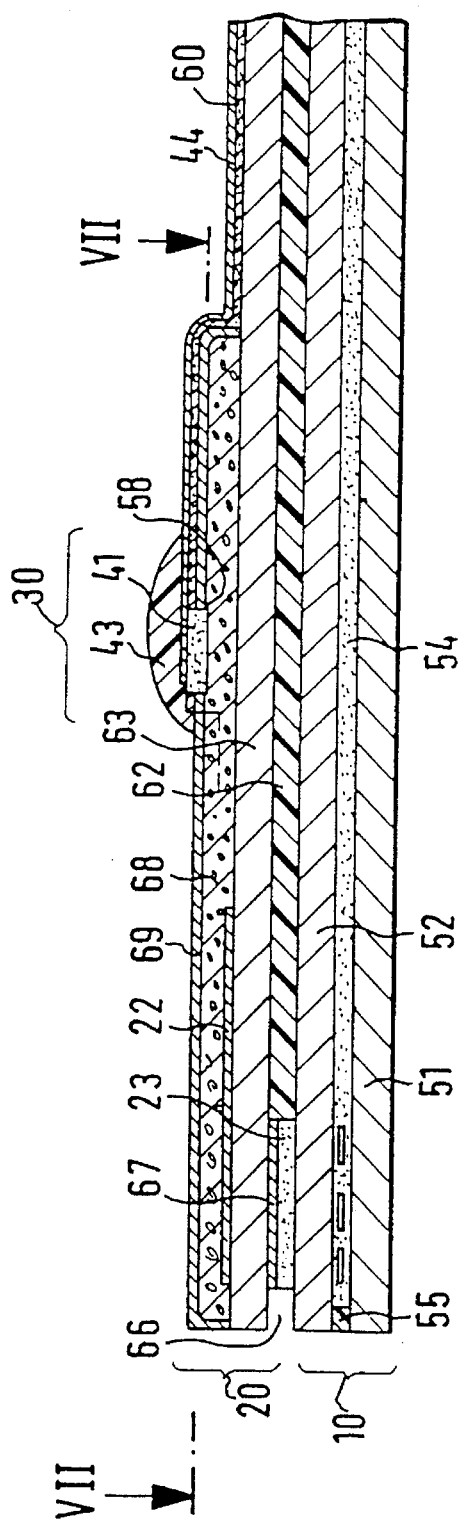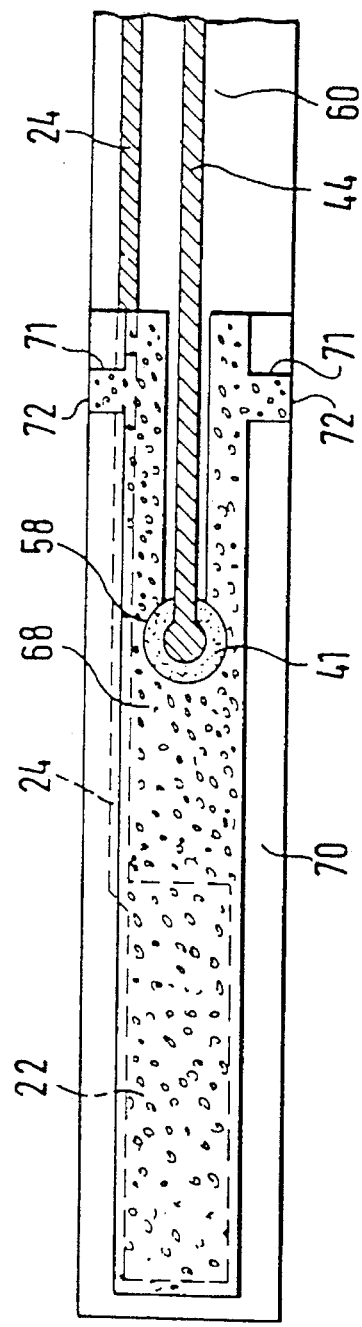

5,505,837

SENSOR ARRANGEMENT FOR DETERMINING GAS COMPONENTS AND/OR GAS CONCENTRATIONS OF GAS MIXTURES

BACKGROUND OF THE INVENTION

1. Field of the Invention

The invention is based on a sensor arrangement for determining gas components and/or gas concentrations in gas mixtures according to the preamble of the main claim.

2. Description of the Related Art

A generic sensor arrangement for determining CO concentrations in which a pump cell pumps oxygen to a measuring element is known from Sensors and Actuators B, 9 (1992), pp. 233–239. The measuring element in this instance is disposed in a measuring chamber without a defined reference to the pump cell and the gas mixture. It is only required that a sufficient oxygen concentration be present at the measuring element. It was determined that the resistance value of an $SnO_2$ semiconductor gas sensor is three orders of magnitude greater in CO in air with 21% $O_2$ than in CO in $N_2$.

SUMMARY OF THE INVENTION

The present invention thus provides a sensor arrangement for determining gas components and/or gas concentrations of gas mixtures, particularly of CO, $NO_x$ and HC in exhaust gases of internal combustion engines, having a measuring element which has a sensitive region and having a pump cell that includes pump electrodes which are disposed on a solid electrolyte and which effect an oxygen transfer to the measuring element, characterized in that the pump cell and the measuring element are disposed so as to be spatially separated from one another such that they are located in different temperature zones during operation of the sensor arrangement.

The sensor arrangement according to the invention has the advantage of the provision of a good galvanic separation and thermal decoupling of the measuring element with respect to the pump cell. This is significant because considerably higher temperatures are necessary to operate the pump cell than the measuring element. Moreover, the object of the pump cell is to pump sufficient oxygen to the measuring element. Therefore, no feedback takes place between the pump cell and the measuring element. In this respect the galvanic separation of the pump cell and the measuring element is important. Relocating the measuring element in colder regions ultimately ensures that the measured gas is exposed to the least possible pre-catalysis. The integrated design of the sensor arrangement ultimately ensures that sufficient oxygen for eliminating the oxygen cross-sensitivity is present at the sensitive region of the measuring element.

Advantageous refinements and improvements of the sensor arrangement disclosed in the main claim are possible by means of the measures outlined in the dependent claims.

A sensor arrangement according to the invention may be characterized in that the pump cell and the measuring element are connected to one another by way of a diffusion segment via which the oxygen can diffuse from the pump cell to the measuring element. Such a sensor arrangement may be constructed as a layer system which includes at least one oxygen-ion-conducting, solid electrolyte ceramic for the pump cell, that the diffusion segment is integrated in the layer system, and that the diffusion segment employs a diffusion opening toward the measuring element, by way of which the oxygen pumped by the pump cell can be supplied to the measuring element. In such a sensor arrangement, the diffusion opening may be a recess cut into a cover film, in which opening the measuring element is disposed with its sensitive region. Such a sensor arrangement may be characterized in that the diffusion opening is cut into a cover layer surrounding the diffusion segment in a gas-tight manner, and that a porous insulating layer on which the measuring element is disposed with its sensitive region is located above the diffusion opening. The measuring element may be a semiconducting gas sensor.

Alternatively, the sensor arrangement may be characterized in that the diffusion opening is cut into a cover layer surrounding the diffusion segment in a gas-tight manner, and that the measuring element is an electrochemical measuring cell that is positioned with its sensitive region in the diffusion opening. A measuring electrode may be inserted in the diffusion opening, and that the inner pump electrode serves as a reference electrode for the measuring cell. Such a sensor arrangement may be characterized in that the sensitive region of the measuring cell is covered by a gas-tight cover, and that the measured gas can be supplied to the sensitive region by way of the diffusion layer, wherein the diffusion layer is in contact with the measured gas by way of at least one measured gas opening. The measured gas opening may be essentially located in a temperature zone of the sensor arrangement in which the measured gas is exposed to a minimum pre-catalysis. The diffusion segment may be a porous diffusion layer guided toward the measuring element or may be a diffusion conduit extending from the pump cell to the measuring element. The measuring element may be disposed with respect to the diffusion segment in such a way, and the pump cell is configured in such a way, that an oxygen surplus is present at the sensitive region of the measuring element. The pump cell and the measuring element respectively may employ separate heating elements that can be adapted in their heat output to the respective operating temperature. A particularly cost-effective design is achieved with a laminate stack of ceramic films that includes at least one ion-conducting ceramic for the pump cell and in which the measuring element is positioned at a lateral distance from the pump cell. The oxygen transport between the pump cell and the measuring element takes place by way of a diffusion segment that is integrated into the laminate stack and can be configured as an open conduit or a porous filling. A resistance sensor of doped $SnO_2$ configured in thick-layer technology has proven to be a particularly suitable measuring element. An electrochemical measuring cell is also suitable as a measuring element. An even better thermal decoupling is achieved when the measured gas is supplied to the sensitive region of the measuring element by way of a lateral diffusion segment, and the direct contact of the measuring element with the measured gas is interrupted by a gas-tight layer. This measure is useful because the measured gas is not pre-catalyzed and the oxygen cannot diffuse unimpaired into the measured gas by way of the sensitive region.

BRIEF DESCRIPTION OF THE DRAWINGS

Three embodiments of the invention are illustrated in the drawings and described in detail in the following description.

3 is a sectional representation corresponding to line III—III in FIG. 1, FIG. 6 is a longitudinal section through a sensor arrangement of the invention according to a third embodiment, and FIG. 7 is a section in the plane of the layer corresponding to the line VII—VII of FIG. 6.

DESCRIPTION OF THE PREFERRED EMBODIMENTS

Figure 1:
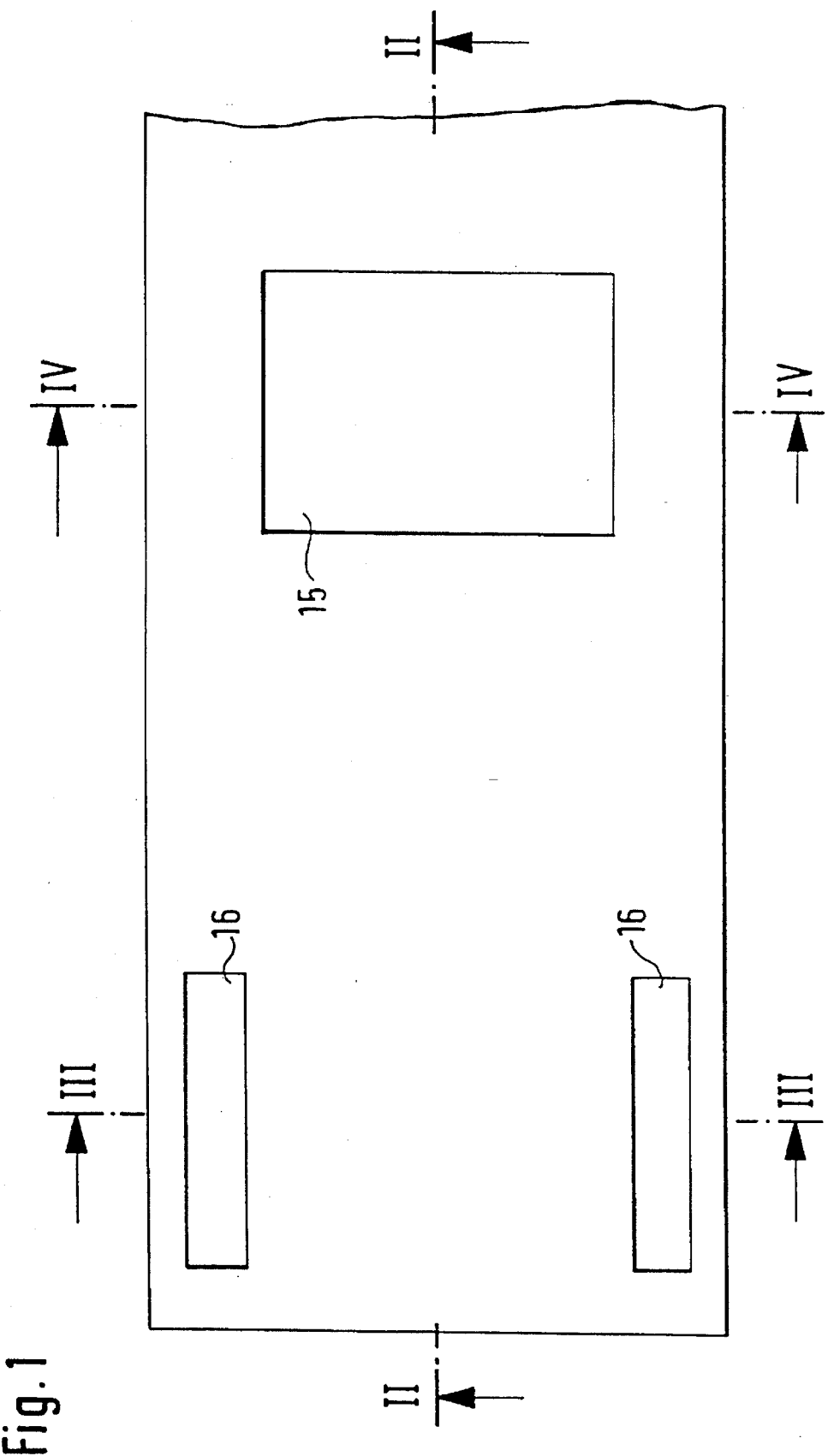
FIG. 1 is a top view of a first embodiment of a sensor arrangement according to the invention.
Figure 2:
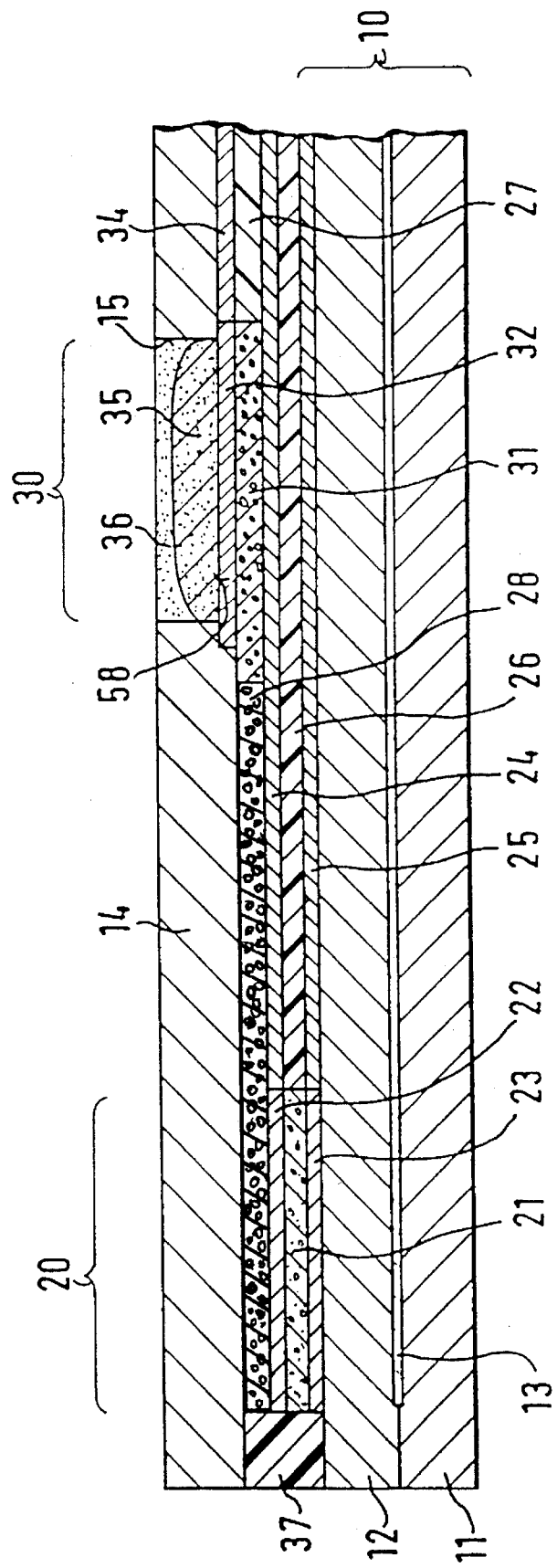
FIG. 2 is a longitudinal section corresponding to lines II—II of FIG. 1, FIG.
Figure 3:
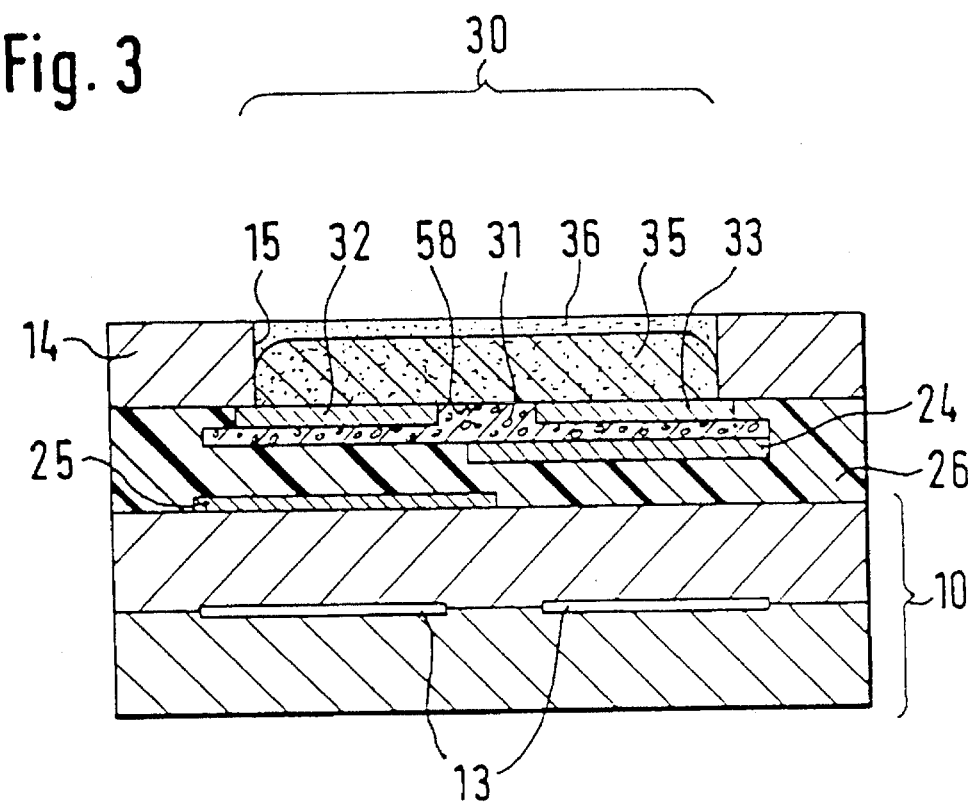

A first embodiment is illustrated in FIGS. 1 through 4. The sensor arrangement has a pump cell 20 and a measuring element 30. A ceramic substrate 10 is configured with a first $Al_2O_3$ film 11 and a second $Al_2O_3$ film 12, between which a resistance heater 13 is disposed. As ensues from FIGS. 3 and 4, the conductor tracks of the resistance heater 13 under the pump cell 20 and the measuring element 30 are dimensioned differently. Because of this, they are heated differently in these zones. It is advisable for the temperature at the pump cell 20 to be approximately 700° C. and approximately 500° C. at measuring element 30.

An outer pump electrode 23 that has a conductor track 25 is disposed on the second $Al_2O_3$ film 12. A porous, oxygen-ion-conducting, solid electrolyte layer 21 of, for example, yttrium-stabilized $ZrO_2$, is located on the outer pump electrode 23. An insulating layer 26 of, for example, $Al_2O_3$ lies above the conductor track 25. The insulating layer 26 is configured, for example, to be of the same thickness as the porous solid electrolyte layer 21. Located on the porous, solid electrolyte layer 21 is an inner pump electrode 22, which is connected to a further conductor track 24 that is guided over the insulating layer 26.

Also provided is a cover film 14, which is likewise made of, for example, $Al_2O_3$. According to FIG. 1, a recess 15, in which the measuring element 30 is inserted, as described later, is located in the cover film 14, at a lateral distance from the pump cell 20. Moreover, two openings 16 located opposite one another are cut into the cover film 14; according to FIG. 4, these openings terminate into a conduit 17 that extends at a right angle to the openings and extends to the side of the pump cell 20. In the present embodiment, the conduits 17 must be guided past the outer pump electrode 23, because the solid electrolyte layer 21 of the pump cell 20 separates the opening 16 and the diffusion conduit 28 in a gas-tight manner. The sensor arrangement is encompassed by a gas-tight frame 37 between ceramic substrate 10 and cover layer 14.

A porous insulating layer 31, for example of $Al_2O_3$, is disposed on the insulating layer 26 and partially on the electrode supply line 24, i.e., conductor track 24, beneath the recess 15. At the same time, the recess 15 forms a diffusion opening 58 toward the insulating layer 31 for the oxygen pumped by the pump cell 20. Two adjacent measuring electrodes 32, 33 are positioned on the insulating layer 31. Opposite the pump cell 20, a further insulating layer 27 adjoins the insulating layer 31; conductor tracks 34 for the measuring electrodes 32, 33 are guided on this further insulating layer. A semiconducting metal oxide layer 35, for example of $SnO_2$, is disposed above the two measuring electrodes 32, 33 in such a way that it at least covers the surface of the recess 15 or the diffusion opening 58. A porous protective layer 36, for example, of $Al_2O_3$ or Mg-spinel (FIGS. 2 and 3) is located above the metal oxide layer 35.

Figure 4:
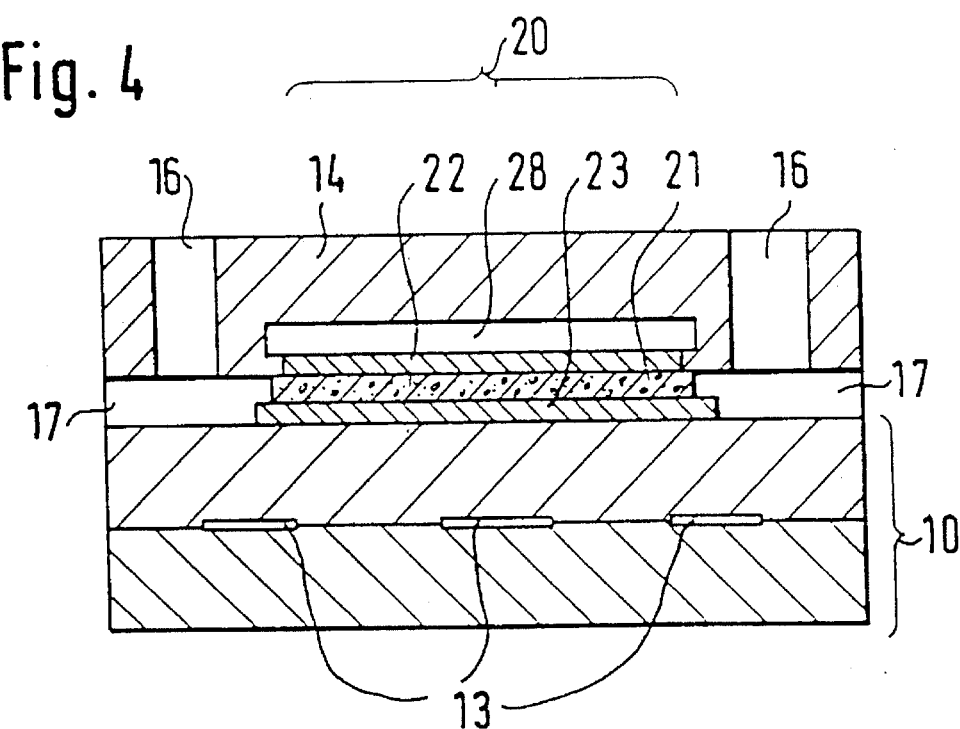
FIG. 4 is a cross-section corresponding to line IV—IV of FIG. 1.

A diffusion conduit 28 that extends laterally from above the inner pump electrode 22 to the porous insulating layer 31, beneath the measuring element 30, is located between cover film 14 on the one side and the insulating layer 26 and the conductor track 24 on the other side. The oxygen pumped from the pump cell 20 to the measuring element 30 diffuses via the diffusion conduit 28. While the diffusion conduit 28 may be a chamber as shown in FIG. 4, it is likewise possible to configure the diffusion conduit 28 as a porous diffusion layer 28 as shown in FIG. 1.

Figure 5:
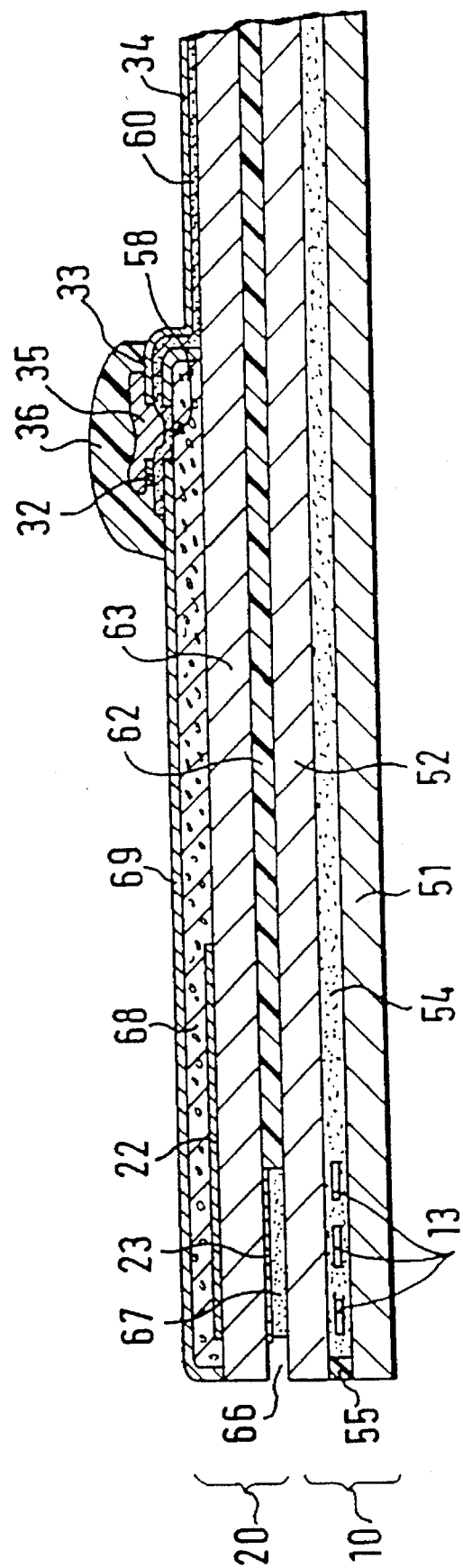
FIG. 5 is a longitudinal section through a sensor arrangement of the invention according to a second embodiment.

FIG. 5 shows a second embodiment, in which the ceramic substrate 10 is formed from two solid electrolyte films 51 and 52, and in which the resistance heater 13 is embedded into a porous heater insulation 54 between the two solid electrolyte films 51, 52. For sealing purposes, the heater insulation 54 is encompassed by a gas-tight frame 55. An insulating separation layer 62, for example, of $Al_2O_3$, is disposed on the ceramic substrate 10; it leaves open a surface in the region of the narrow front face, which surface forms a diffusion gap 66. A porous diffusion member 67, for example, in layer form, is disposed in the diffusion gap 66.

A further solid electrolyte film 63, on which the pump cell 20 is configured in the region of the diffusion member 67, lies above the separating layer 62. The outer pump electrode 23, whose conductor track, not shown, is guided between the separating layer 62 and the solid electrolyte film 63, lies above the diffusion member 67. The inner pump electrode 22 is disposed on the large surface of the solid electrolyte film 63, opposite the outer pump electrode 23. The inner pump electrode 22 likewise has a conductor track, not shown, that is guided on the solid electrolyte film 63.

A porous diffusion layer 68 is located on the solid electrolyte film 63, the porous diffusion layer 68 being guided over the inner pump electrode 22 to the measuring element 30 disposed at a lateral distance from the pump cell 20. The porous diffusion layer 68 is covered by a gas-tight cover layer 69. Instead of the measuring element 30, the cover layer 69 has the diffusion opening 58.

In the present embodiment, as in the first embodiment, a semiconductor gas sensor is used as the measuring element 30. For galvanic separation, a porous insulating layer 60, which is further guided over the solid electrolyte film 63, for example, is laid above the opening 58. The two measuring electrodes 32, 33, whose electrode conductor tracks 34 are guided further over the insulating layer 60, are disposed on the insulating layer 60. The semiconducting metal oxide layer 35 is disposed above the measuring electrodes 32, 33. Finally, the porous protective layer 36 is located above the metal oxide layer 35.

FIGS. 6 and 7 show a third embodiment. In this instance, with regard to the ceramic substrate 10 and the pump cell 20, the sensor arrangement is designed in the same way as the sensor arrangement according to FIG. 5. In contrast to the embodiment according to FIG. 5, however, the measuring element 30 is an electrochemical measuring cell that operates according to the Nernst principle. A measuring electrode 41, which is connected to a measuring electrode conductor track 44, is inserted into the diffusion opening 58. The measuring electrode conductor track 44 is guided over the insulating layer 60, the insulating layer extending up to the measuring electrode 41.

According to FIG. 7, the conductor track 24 of the inner pump electrode 22 likewise lies on the insulating layer 60. The measuring electrode 41 is provided with a gas-tight cover 43. A glass which melts during sintering, for example, is suitable as the gas-tight cover 43.

In this embodiment, the inner pump electrode 22 simultaneously forms the reference electrode for the electrochemical measuring cell 30. The oxygen-ion supply between the measuring electrode 41 and the reference electrode takes place by way of the porous diffusion layer 68, which is made of oxygen-ion-conducting material, for example $ZrO_2$. In this embodiment, the oxygen surplus necessary for the elimination of the oxygen cross-sensitivity is already effective at the inner pump electrode 22.

In this embodiment, the supply of the measured gas does not take place directly to the sensitive region of the measuring cell 30, but, exactly as with the oxygen pumped by the pump cell 20, by way of the diffusion layer 68. The cover layer 69 forms a gas-tight frame 70 around the porous diffusion layer 68, in which frame recesses 71 are provided for supplying the measured gas to, for example, two opposite sides. The porous diffusion layer 68 extends into the recesses 71, so that the recesses 71 respectively form a measured gas opening 72. The recesses 71 are advisably further from the pump cell 20 than the measuring cell 30. Because of this, the measured gas opening 72 lies even further from the pump cell 20 than the measuring cell 30, and thus even further in the colder region. The intent of this is for the measured gas to be less catalyzed. An excessive catalysis effect would result in a precombustion of the measured gas, so no realistic gas conditions would be present at the sensitive region of the measuring element 30.

It is also possible to configure the diffusion conduit 68 as a porous material only in the region of the measuring cell 30, and otherwise as a hollow chamber.

To operate the sensor arrangement, a pump voltage is applied to the pump electrodes 22, 23, and a constant oxygen partial pressure is established at the inner pump electrode 22 by means of a known control circuit, as described, for example, in the SAE publication 86 04 08. According to the invention, the oxygen partial pressure is established to excess compared to the partial pressure of the gas components to be measured. For example, the oxygen partial pressure is selected between 2 and 10% of the total pressure of the measured gas. The constant oxygen partial pressure also corresponds to the oxygen partial pressure applied to the measuring element 30.

In the use of the sensor arrangement, either the pump cell 20 and the measuring element 30 can be immersed so far into the measured gas that the measured gas opening 72 is exposed to the measured gas, or in the third embodiment according to FIG. 6 and 7. In this instance the pump cell 20 pumps away molecular oxygen or oxygen from oxygen-containing compounds from the measured gas by way of the outer pump electrode 23. It is, however, equally standard practice to bring only the measuring element 30 into contact with the measured gas, and to expose the pump cell 20, with the diffusion gap 66, to a reference from of which the oxygen is pumped.

The described sensor arrangement is preferably configured in thick-film technology. The screen-printing technology conventionally used for this has been long known.

What is claimed is:

1. A sensor arrangement for determining at least one of gas components and gas concentrations of gas mixtures including CO, $NO_x$ and HC in exhaust gases of internal combustion engines, comprising:

a measuring element which has a sensitive region; and a pump cell that includes a solid electrolyte and inner and outer pump electrodes which are opposingly disposed at least on the solid electrolyte and which effect an oxygen transfer to the measuring element, wherein the pump cell and the measuring element are spatially separated from one another, in a lateral arrangement and are located in different temperature zones during operation of the sensor arrangement, and are connected to one another by a diffusion segment through which oxygen diffuses from the pump cell to the measuring element during operation of the sensor arrangement.

2. The sensor arrangement according to claim 1, wherein the sensor arrangement is a layer system in which the solid electrolyte is at least one oxygen-ion-conducting, solid electrolyte ceramic, wherein the diffusion segment is integrated into the layer system, and wherein oxygen pumped by the pump cell is supplied to the measuring element via the diffusion segment and via a diffusion opening provided, near the measuring element.

3. The sensor arrangement according to claim 2, further comprising a cover film, wherein the diffusion opening is a recess defined in the cover film, and wherein the measuring element including the sensitive region is disposed in the diffusion opening.

4. The sensor arrangement according to claim 3, wherein the measuring element is a semiconducting gas sensor.

5. The sensor arrangement according to claim 2, further comprising a cover layer which surrounds the diffusion segment in a gas-tight manner, wherein the diffusion opening is defined in the cover layer, and wherein a porous insulating layer is provided above the diffusion opening and onto which porous insulating layer is disposed the measuring element with the sensitive region.

6. The sensor arrangement according to claim 2, further comprising a cover layer surrounding the diffusion segment in a gas tight manner, wherein a diffusion opening is defined in the cover layer, and wherein the measuring element is an electrochemical measuring cell that is positioned with the sensitive region in the diffusion opening.

7. The sensor arrangement according to claim 6, further comprising a measuring electrode which is inserted into the diffusion opening, and wherein the inner pump electrode serves as a reference electrode for the measuring cell.

8. The sensor arrangement according to claim 7, further comprising a gas-tight cover which covers the sensitive region of the measuring cell and in which are defined recesses which define at least one measured gas opening, wherein the diffusion layer extends into the recesses defined in the gas-tight cover layer whereby measured gas is supplied to the sensitive region via the diffusion layer, and wherein the diffusion layer is in contact with the measured gas via the at least one measured gas opening.

9. The sensor arrangement according to claim 8, wherein the at least one measured gas opening is located in a temperature zone of the sensor arrangement in which the measured gas is exposed to a minimum pre-catalysis.

10. The sensor arrangement according to claim 8, wherein the diffusion segment is a porous diffusion layer.

11. The sensor arrangement according to claim 1, wherein the diffusion segment is a diffusion conduit.

12. The sensor arrangement according to claim 1, wherein the measuring element, the diffusion segment, and the pump cell are positioned so that an oxygen surplus is present at the sensitive region of the measuring element during operation of the sensor arrangement.

13. The sensor arrangement according to claim 1, wherein the pump cell and the measuring element respectively employ separate heating elements, each heating element having a respective heat output, which respective heat outputs provide respective operating temperatures.

14. The sensor arrangement according to claim 1, wherein the pump cell and the measuring element have respective temperature zones, each respective temperature zone having a temperature, and wherein the temperature of the temperature zone of the pump cell is about 700° C. and the temperature of the temperature zone of the measuring element is about 500° C.

15. The sensor arrangement according to claim 1, wherein the sensor arrangement further comprises at least one heating device for establishing respective operating temperatures for the pump cell and the measuring element and providing the different temperature zones.

16. The sensor arrangement according to claim 15, wherein the sensor arrangement is an assembly of layers having a ceramic substrate within which the at least one heating device is embedded.

17. The sensor arrangement according to claim 15,
wherein the sensor arrangement is an assembly of layers extending in a lateral direction parallel to the surface and in a vertical direction perpendicular to the surface,
wherein at least the pump cell and the measuring element are integrated within the assembly of layers, and are respectively disposed in the lateral direction so that the pump cell and the measuring cell are spatially separated from one another and whereby the pump cell and the measuring element are located in the different temperature zones during operation of the sensor arrangement, and
wherein the diffusion segment extends in the lateral direction from the pump cell to the measuring element.

18. The sensor arrangement according to claim 17, wherein the pump cell and the measuring element have respective temperature zones, each respective temperature zone having a temperature, and wherein the temperature of the temperature zone of the pump cell is about 700° C. and the temperature of the temperature zone of the measuring element is about 500° C.

* * * * *